(12) United States Patent
Almulhim

(10) Patent No.: US 11,819,213 B1
(45) Date of Patent: Nov. 21, 2023

(54) TRIPLE ENDOSCOPIC LOOP FOR LAPAROSCOPIC APPENDECTOMY

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/172,066

(22) Filed: Feb. 21, 2023

(51) Int. Cl.
*A61B 17/12* (2006.01)
*A61B 17/00* (2006.01)

(52) U.S. Cl.
CPC ........... *A61B 17/12013* (2013.01); *A61B 2017/00823* (2013.01)

(58) Field of Classification Search
CPC ........... A61B 17/0469; A61B 17/12; A61B 17/12009; A61B 17/12013; A61B 17/3205; A61B 17/32056; A61B 2017/00823; A61B 2017/0475; A61B 2017/0477; A61B 2017/0496
See application file for complete search history.

(56) References Cited

U.S. PATENT DOCUMENTS

| | | | |
|---|---|---|---|
| 5,190,554 A * | 3/1993 | Coddington, III | A61B 17/00234 606/1 |
| 5,284,488 A | 2/1994 | Sideris | |
| 5,609,597 A * | 3/1997 | Lehrer | A61B 17/12013 606/139 |
| 5,643,289 A | 7/1997 | Sauer et al. | |
| 6,120,513 A * | 9/2000 | Bailey | A61B 17/12013 606/139 |
| 6,350,269 B1 | 2/2002 | Shipp et al. | |
| 8,216,234 B2 * | 7/2012 | Long | A61B 18/14 606/50 |
| 11,419,602 B2 | 8/2022 | Zentgraf | |
| 11,471,152 B2 | 10/2022 | Heneveld | |
| 2010/0312260 A1 * | 12/2010 | Herron | A61B 17/064 606/144 |
| 2014/0350566 A1 * | 11/2014 | Emmanouilidis | A61B 17/1114 606/113 |

FOREIGN PATENT DOCUMENTS

KR 102320419 B1 * 11/2021 ....... A61B 17/12013

OTHER PUBLICATIONS

English machine translation of KR102320419B1 (Year: 2021).*

* cited by examiner

*Primary Examiner* — Darwin P Erezo
*Assistant Examiner* — Christian D Knauss
(74) *Attorney, Agent, or Firm* — Nath, Goldberg & Meyer; Richard C. Litman

(57) ABSTRACT

The triple endoscopic loop for laparoscopic appendectomy includes an elongated cannula having a proximal end and a distal end. A first loop is located at the distal end and secures the base of the appendix at a first point. A second loop is spaced apart from the first loop at the distal end, and secures the base of the appendix at a second point. A third loop is spaced apart from the second loop at the distal end, and secures the body of the appendix at a third point. A handle is located at the proximal end. The handle is connected to the first loop, the second loop and the third loop such that when the handle is pulled away from the cannula, the loops further secure the appendix at the first point, the second point, and the third point, respectively.

4 Claims, 2 Drawing Sheets

TRIPLE ENDOSCOPIC LOOP FOR LAPAROSCOPIC APPENDECTOMY

BACKGROUND

1. Field

The present disclosure relates to laparoscopic surgery, and particularly to a triple endoscopic loop for laparoscopic appendectomy.

2. Description of the Related Art

Laparoscopic surgery is a surgical procedure that allows access to the inside of a patient's body without making a large incision. This type of surgery is sometimes called keyhole surgery, since it only requires a small incision and is minimally invasive compared to other types of surgeries. Small incisions are made in the patient to allow access into the body. A tube or port is placed through the incision and into the body. Gas is pumped into the body through the tube. A laparoscope, that includes a small camera and light, is inserted into the body, allowing for images to be displayed on a monitor. Small surgical tools can then be inserted into the body through other small incisions, allowing for medical procedures to be performed.

It can be challenging to perform laparoscopic surgery due to the small size of the incisions. The surgical tools must be small, and it can be difficult to operate the tools in such a confined space. The patient may also prefer not to have so many incisions.

An appendectomy is a common emergency surgery requiring the removal of the appendix, which is a small thin pouch attached to the large intestine. The appendix is located in the lower right part of the belly. Removal of the appendix can become necessary when the appendix becomes sore, swollen and/or infected.

Performing laparoscopic surgery to remove the appendix will require incisions in the lower right part of the belly to pump gas into the body and insert a laparoscope. Surgical tools that tie off the appendix from the large intestine and to remove the appendix will then need to be inserted into the body. Three endoscopic loops are sometimes used to secure the base of the appendix before cutting. The surgery can be difficult because of the number of surgical instruments that need to be used. It will take up a considerable amount of space and will require multiple incisions. The number of surgical instruments will also be hard to handle.

Thus, a triple endoscopic loop for laparoscopic appendectomy solving the aforementioned problems is desired.

SUMMARY

The triple endoscopic loop for laparoscopic appendectomy reduces the number of surgical instruments needed in laparoscopic surgeries, such as an appendectomy, and also simplifies the procedure. This is accomplished using two loops to secure the base of an appendage, such as an appendix, and a third loop to secure the contents.

The triple endoscopic loop for laparoscopic appendectomy, in one embodiment, includes an elongated cannula having a proximal end and a distal end. A first loop is located at the distal end and secures an appendage at a first point. A second loop is spaced apart from the first loop at the distal end, and secures the appendage at a second point. A third loop is spaced apart from the second loop at the distal end, and secures the appendage at a third point. A handle is located at the proximal end. The handle is connected to the first loop, the second loop and the third loop such that when the handle is pulled away from the longitudinal body the first loop further secures the appendage at the first point, the second loop further secures the appendage at the second point, and the third loop further secures the appendage at the third point.

The first point, in one embodiment, is located at the base of the appendage, the second point is located at a distance on the appendage spaced apart from the first point, and the third point is located at a distance on the appendage spaced apart from the second point.

The first loop, in some embodiments, is spaced apart from the second loop at a distance of 3 mm and the second loop is spaced apart from the third loop at a distance of 5 mm. The elongated cannula is 30 cm long.

The handle includes a first looped handle and a second looped handle spaced apart from the first looped handle at the proximal end of the longitudinal body.

The first and second looped handles extend through a 10 mm opening in the proximal end of the longitudinal body.

The device in alternate embodiments further includes wires or suture material that extend from the handle to the first loop, the second loop, and the third loop such that when the handle is pulled away from the longitudinal body the first loop further secures the appendage at the first point, the second loop further secures the appendage at the second point, and the third loop further secures the appendage at the third point by securing knots to close the distal loops.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The triple endoscopic loop for laparoscopic appendectomy incudes three loops that can be inserted at one time through a single laparoscopic port during a laparoscopic appendectomy. The appendectomy, in some instances, makes use of two endoscopic loops to secure the base of the appendix, and a third loop to secure the contents of the appendix before cutting. A device that inserts all three loops at once significantly simplifies the surgery by reducing the number of surgical tools needed.

Figure 1:
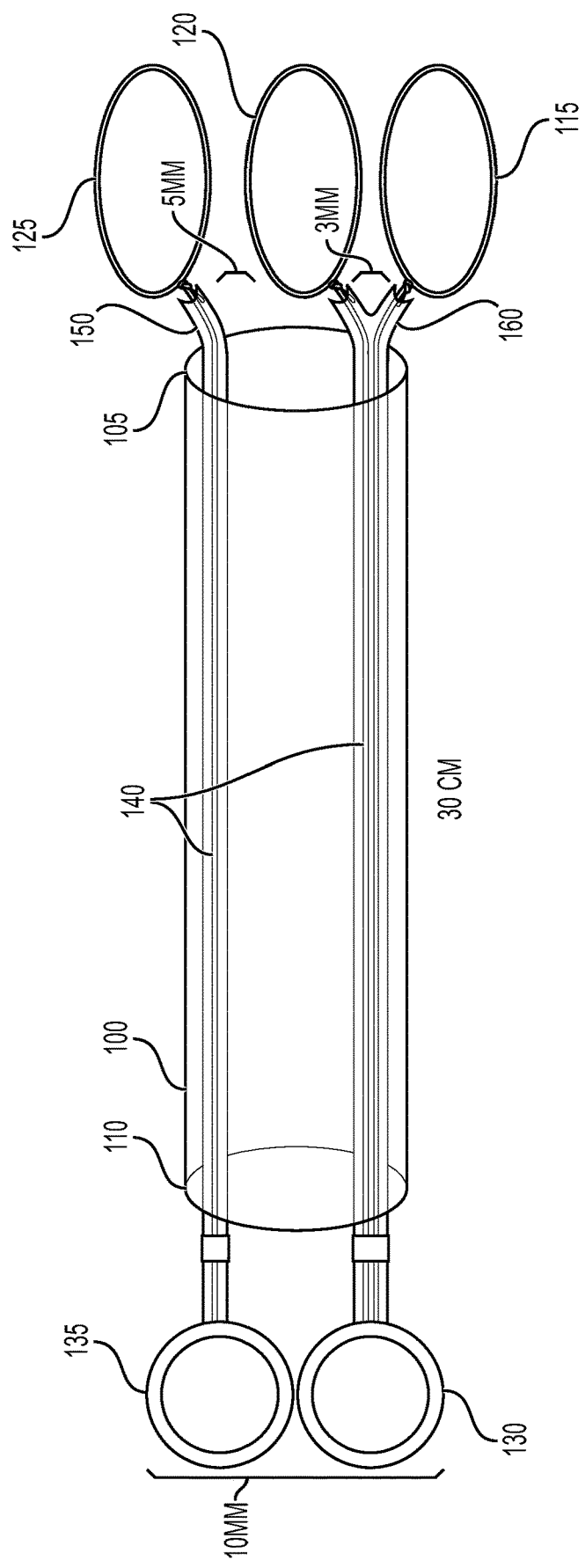
FIG. 1 is a diagrammatic side view of a triple endoscopic loop for laparoscopic appendectomy.

FIG. 1 is an illustration of an exemplary embodiment of the triple endoscopic loop for appendectomy that includes an elongated cannula 100 having a distal end 105 and a proximal end 110. The distal end 105 includes a first loop 115, a second loop 120 and a third loop 125 (loops 115, 120, 125). The proximal end 110 includes a first looped handle 130 and a second looped handle 135 (handle 130,135). Wires or lengths of suture material 140 extend through sheathes 150, 160 inside the cannula 100 to connect the handles 130, 135 to the loops 115, 120, 125.

The length of the cannula 100, in some embodiments, is 30 cm. The first loop 115 is spaced apart from the second loop 120 by a distance of 3 mm, and the third loop 125 is spaced apart from the second loop 120 by a distance of 5 mm. The diameter of the cannula 100 may be 10 mm. The wires or lengths of suture material 140 extend from the handle (130, 135) to the loops (115, 120, 125). The first loop 115, the second loop 120 and the third loop 125 get smaller and tighten knots in the loops 115, 120, and 125 when the handle (130,135) is pulled away from the longitudinal body 100. The loops 115 and 120 extend from a single sheath 160 and are intertwined so that pulling the handle 130 simultaneously tightens the knot for loop 115 and the knot for loop 120 to ligate the base of the appendix at two points separated by about 4 mm. The loop 125 extends from a separate sheath 150 so that loop 125 can be separately secured around the body of the appendix, and the knot for loop 125 can be tightened separately by pulling handle 135 to secure the contents of the appendix.

Figure 2:
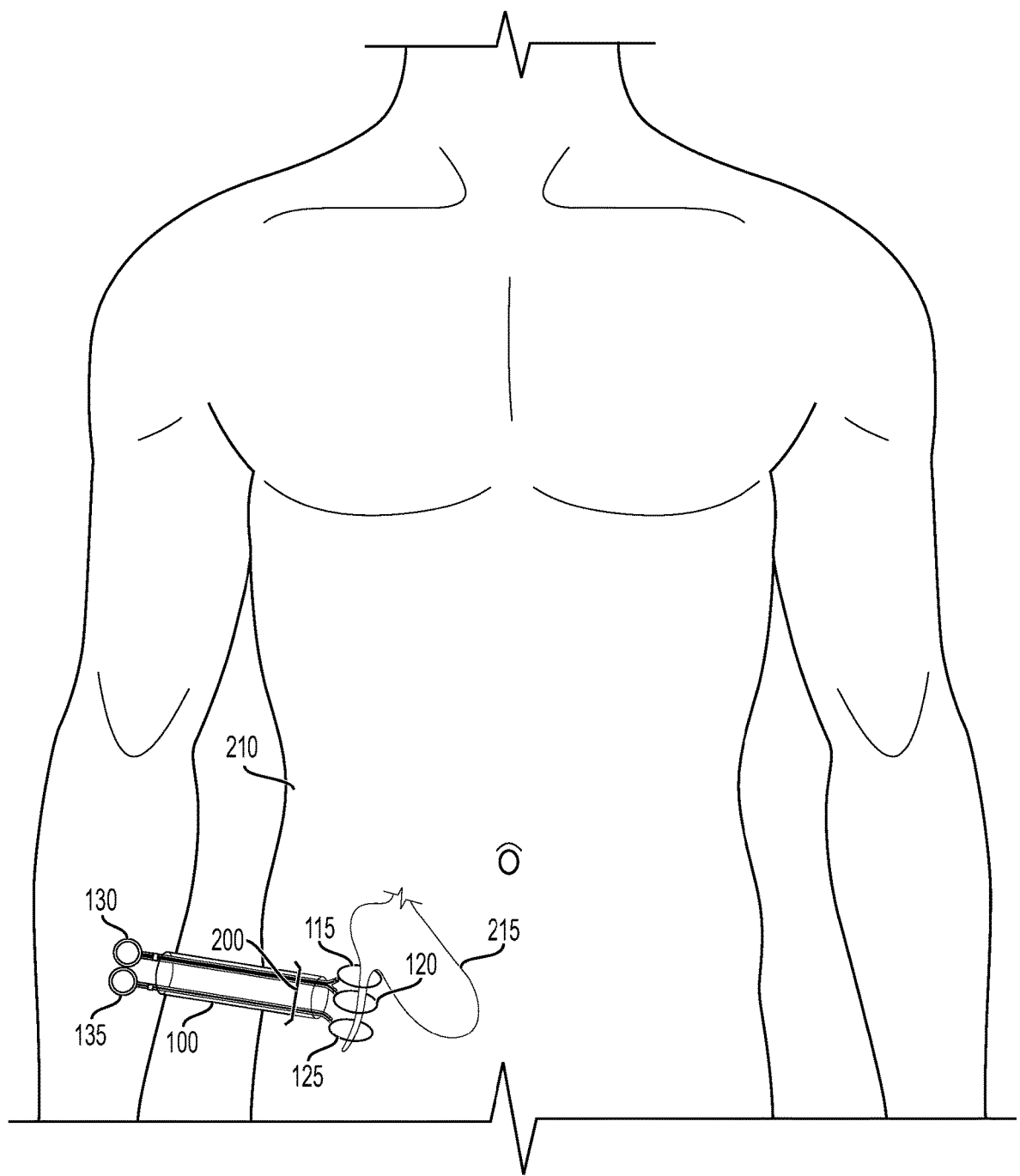
FIG. 2 is an environmental perspective view, largely schematic, of the triple endoscopic loop for appendectomy in use.

FIG. 2 is an illustration of the triple endoscopic loop for appendectomy inside of a patient. The double endoscopic loop is used for the ligation of the appendicular stump or base of the appendix during a laparoscopic appendectomy. After the dissection of the mesoappendix, the base of the appendix is prepared for ligation. An incision 200 is initially made in the body 210 of the patient. The cannula 100 of the triple endoscopic loop is inserted through a laparoscopic port placed in the incision 200 into the body 210. The first loop 115 and the second loop 120 extend inside the body 210 and are placed around the appendix 215 at the base of the appendix. The third loop 125 secures the appendix at an end of the appendix opposite the base. The handles 130,135 remain outside the body 210 and are accessible to the surgeon performing the appendectomy. The first looped handle 130 and the second looped handle 135 are gripped by the surgeon and pulled away from the longitudinal body 100 tightening the first loop 115 and second loop 120 to secure the appendix base, and the third loop to secure a portion of the appendix at an end opposite of the base to secure the contents of the appendix before cutting. As the handles 130,135 are pulled away from the cannula 100, the loops 115,120,125 get smaller and the knots are tightened. In some embodiments when one of the loops 115,120,125 can no longer be tightened, the other loops are allowed to tighten. In other embodiments, the loops are restricted from tightening when one loop can no longer be tightened.

The distance between the first loop 115 and the second loop 120, in some embodiments, is 3 mm and the distance between the third loop 125 and the second loop 120 is 5 mm. A cutting mechanism is then used to cut the appendix between the first loop 115 and the second loop 120. In an ideal case, the loops are tightened simultaneously until they cannot be further tightened.

It is to be understood that the triple endoscopic loop for laparoscopic appendectomy is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A triple endoscopic loop for laparoscopic appendectomy, the triple endoscopic loop comprising:
   an elongated longitudinal cannula having a proximal end and a distal end, the cannula being adapted for insertion through a laparoscopic port;
   a first loop located at the distal end of the cannula, the first loop being adapted for attachment to a base of an appendix, the first loop having a first knot for ligating the base of the appendix at a first point;
   a second loop spaced apart from the first loop at the distal end of the cannula, the second loop being adapted for attachment to the base of the appendix, the second loop having a second knot for ligating the base of the appendix at a second point spaced apart from the first point;
   a third loop spaced apart from the second loop at the distal end, the third loop being adapted for attachment to a body of the appendix, the third loop having a third knot for tightening the third loop around the body of the appendix to control contents of the appendix; and
   at least one handle located at the proximal end of the cannula, the at least one handle being connected to the first loop, the second loop and the third loop such that when the at least one handle is pulled away from the longitudinal cannula, the first knot is tightened so that the first loop ligates the base of the appendix at the first point, the second knot is tightened so that the second loop ligates the base of the appendix at the second point, and the third knot is tightened to secure the third loop around the body of the appendix,
   wherein said at least one handle comprises:
   a first looped handle and a second looped handle;
   a first sheath and a second sheath extending through said cannula from the proximal end to the distal end;
   a first length of suture material extending through the first sheath between the first looped handle and the third loop, the first looped handle tightening the third knot when the first looped handle is pulled in order to tighten the third loop around the body of the appendix; and
   a second length of suture material extending through the second sheath between the second looped handle and the first and second knots, the second looped handle simultaneously tightening the first and second knots to ligate the base of the appendix at the first and second spaced apart points when the second looped handle is pulled, whereby the base of the appendix may be severed between the first and second spaced apart points for removal of the appendix.

2. The triple endoscopic loop as recited in claim 1, wherein the first loop is spaced apart from the second loop at a distance of 3 mm and the second loop is spaced apart from the third loop at a distance of 5 mm.

3. The triple endoscopic loop as recited in claim 1, wherein said cannula is 30 cm long.

4. The triple endoscopic loop as recited in claim 1, wherein said cannula has a diameter of 10 mm.

* * * * *